US011574245B2

(12) United States Patent
Dao et al.

(10) Patent No.: US 11,574,245 B2
(45) Date of Patent: Feb. 7, 2023

(54) METHOD FOR SECURING A MACHINE LEARNING BASED DECISION SYSTEM

(71) Applicant: THALES DIS FRANCE SAS, Meudon (FR)

(72) Inventors: Frédéric Dao, Gemenos (FR); Thomas Dandelot, Gemenos (FR); Frédéric Paillart, Gemenos (FR); Frédéric Faure, Gemenos (FR); Fabrice Delhoste, Gemenos (FR)

(73) Assignee: THALES DIS FRANCE SAS, Meudon (FR)

( * ) Notice: Subject to any disclaimer, the term of this patent is extended or adjusted under 35 U.S.C. 154(b) by 383 days.

(21) Appl. No.: 16/640,549

(22) PCT Filed: Jul. 31, 2018

(86) PCT No.: PCT/EP2018/070743
§ 371 (c)(1),
(2) Date: Feb. 20, 2020

(87) PCT Pub. No.: WO2019/038036
PCT Pub. Date: Feb. 28, 2019

(65) Prior Publication Data
US 2020/0219009 A1    Jul. 9, 2020

(30) Foreign Application Priority Data
Aug. 21, 2017  (EP) .................... 17306085

(51) Int. Cl.
*G06N 20/00*   (2019.01)
*G06F 21/44*   (2013.01)
(52) U.S. Cl.
CPC ............ *G06N 20/00* (2019.01); *G06F 21/44* (2013.01)

(58) Field of Classification Search
CPC ............................... G06N 20/00; G06F 21/44
See application file for complete search history.

(56) References Cited

U.S. PATENT DOCUMENTS

| 2017/0227995 A1 | 8/2017 | Lee et al. |
| 2017/0230360 A1 | 8/2017 | Mosenia et al. |
| 2018/0039990 A1* | 2/2018 | Lindemann ............ G06V 40/19 |

OTHER PUBLICATIONS

International Search Report (PCT/ISA/210) and Written Opinion (PCT/ISA/237) dated Sep. 14, 2018, by the European Patent Office as the International Searching Authority for International Application No. PCT/EP2018/070743.
(Continued)

*Primary Examiner* — Shukri Taha
(74) *Attorney, Agent, or Firm* — Marc Boillot—Thales Dis CPL USA, Inc (57) ABSTRACT

A system configured to perform decision tasks carried out by a machine learning engine operates with a machine learning model, and includes a training component for improving the machine learning model, a device for carrying out decisions based on a set of input data, and an interaction interface for switching the machine learning model between training component and a device that includes a model attestation checker. The device performs acquiring input data, and ascertaining at least one machine learning model over the interaction interface. The model attestation checker performs checking if said machine learning model is trusted by a model attestation, and considering, for decision making, only those machine learning models that are trusted. The machine learning engine performs carrying out the decision task for input data by using a trusted machine learning model, and providing a result attestation for the decision output.

15 Claims, 4 Drawing Sheets

(56) References Cited

OTHER PUBLICATIONS

Akbani, et al., "EMLTrust: An enhanced Machine Learning based Reputation System for MANETs", Ad Hoc Networks, Aug. 2011, vol. 10, No. 3, pp. 435-457.

* cited by examiner

METHOD FOR SECURING A MACHINE LEARNING BASED DECISION SYSTEM

FIELD OF THE INVENTION

The present invention relates to a method for securing a machine learning based decision system. The invention also pertains to a device for using said method.

BACKGROUND OF THE INVENTION

Today a growing amount of tasks for which in earlier times human interaction was needed are today fulfilled by automatized system, thanks to so-called artificial intelligence methods, mainly subsumed under "machine learning" systems. Such machine learning system comprise at least a machine learning model which is trained with many input data. Such data may come from various sources, and are supposed to build a link between a subject and a qualification of the subject. E.g. for face recognition hundreds of thousands of pictures of a person are loaded, and the qualification assigns names to such pictures. This assignment is typically done by humans.

But more and more such tasks relate to decisions where people can be really severely impacted depending upon the decision. Such situations may in particular occur in automated systems relating to traffic, e.g. break-assistance, autonomous speedometer with sign detection, up to autonomous driving. In other areas like health and financial analysis this applies as well, as it is known for credibility scoring, access to health care etc. This already indicates the wide range of scenarios where machine learning based decision methods may heavily impact the affected individuals.

It is apparent that such systems may lead to outcomes, where a human decision would most likely come to less impacting decisions. This is in particular true in case of car accidents, that a conscious human driver would be able to avoid.

Furthermore such systems are also due to the heavy impact prone to hacking activities. Should hackers may make themselves empowered to full brake a good share of cars produced by a certain brand at one time, this could costs lives, ruin large enterprises or make them open to blackmailing.

Such hacking activities may affect different areas of the decision making engine, in particular adding malicious data on purpose or modifying hardware car components. Besides common security violations that may affect all kinds of digital systems, for a machine learning based systems additionally manipulation of input data are an additional issue, which need special consideration. Such poisonous measures are called "causative attacks", which are such hacker attacks intended to alter training data for creating a machine learning model. Furthermore altering the machine learning model is another open gate for hackers.

By now only measures are known where such hacking attempts are tried to globally stop or to detect algorithmically if training data are faked. None of both measures can fully cover the risks and lead to accountability when a machine learning based decision was tampered.

Hence it requires not only securing such system as such but to introduce measures to mitigate any other hacking attempt.

It is therefore the goal of present invention to propose a solution for an improved security of machine learning based decision systems.

Further alternative and advantageous solutions would, accordingly, be desirable in the art.

SUMMARY OF THE INVENTION

For this it is according to a first aspect of the invention suggested a method for securing a system being configured to perform decision tasks according to claim 1. It is further suggested according to a second aspect of the invention a device for performing a decision task according to claim 6.

According to the first aspect of the invention it is proposed a method for securing a system being configured to perform decision tasks carried out by a machine learning engine, equipped for operating with at least one machine learning model, the system comprising at least one training component for improving the at least one machine learning model, a device for carrying out decisions based on said machine learning model and a set of input data, and an interaction interface for exchanging said at least one machine learning model between training component and device, wherein the device comprises a model attestation checker, the method comprising the steps of:

for the device:
    acquiring input data,
    ascertaining at least one machine learning model over the interaction interface,
for the model attestation checker:
    checking if said at least one machine learning model is trusted by a model attestation,
    considering by the machine learning engine for said decision making only those machine learning models that are trusted, for the machine learning engine:
    carrying out the decision task for acquired input data by using said at least one trusted machine learning model,
    providing a result attestation for the decision output.

The first aspect of the invention relates to a system for performing decision tasks. Such decisions tasks in particular comprise detections, predictions, ratings or any other task where a plurality of input data are evaluated and analyzed and a result is produced. For doing so, the system comprises a device which is equipped with a machine learning engine. The machine learning engine is configured to employ at least one machine learning model. Furthermore the system comprises at least one sensor, like an optical or acoustical sensor, or any other input means for acquiring a set of input data. The device retrieves the machine learning model from a training component of the system. The training component is a component which is configured to process a plurality of training data, like images, sound files, text files etc., which are accompanied by a qualification. Such qualification marks the respective training data with a certain meaning, or with a rejection of a meaning. That comprises e.g. a picture of a person with a name or other identifier of a person. Alternatively such picture is additionally or alternatively accompanied by a negative qualification, like which person is not visible on the picture, or which situations do not represent a situation which needs a full brake.

The device retrieves the machine learning model from the training component through the interaction interface. In case device and training component are located at different places, this interaction interface is any type of data transfer from the one system component to the other. In case training component and device are situated together, in particular when the training component is part of the device, then an internal access from the machine learning engine to the machine learning model is established. Such access may need an internal copying operation, however it is also encompassed by the invention that the machine learning engine works with the machine learning model at the place of training, in particular while it is continuously trained.

Furthermore it is encompassed by the invention that the machine learning engine is configured to operate with more than one machine learning model. Such is in particular applicable when the decision task might be carried out through a two- (or more) fold approach, e.g. a first categorization, and then a detailed detection. For optical face recognition e.g. a first machine learning model is preferably used to detect if a person is recorded with the optical sensor, like a camera. The second machine learning model is then used for detecting which person is recorded. For doing so results or auxiliary data from the first detection step are exchanged between the first and second detection step.

The goal of the invention is to secure a system for performing such decision tasks. For that the device is further equipped with a model attestation checker. The model attestation checker has the task to figure out if the machine learning model is trustable or not.

For doing so the method of the system is operating that way, that the device ascertains the at least one machine learning model over said interaction interface. Before using the machine learning model however the model attestation checker checks if the machine learning model is trusted thanks to a model attestation.

Such model attestation has the task to confirm the reliability of the machine learning model. The model attestation is preferably issued by the training component. Technically speaking such a model attestation is in a preferred embodiment carried out by a digital signature. The digital signature is according to commonly known methods like DSA a code or file, which is calculated by signing algorithm from the original file—here a representation of the machine learning model and—a signing key. The receiver of the signature can for verification calculate from the received original file the signature and a public key in order to figure out if the file is valid or not. That indicates the integrity of the received original file, that means the file was not changed since signing. Furthermore it is assured that the file was created by the signing party. Effectively the model attestation assures that the machine learning model can be trusted.

Other ways of attestation are also encompassed by the invention, like certificates, a hash etc. and combinations thereof. The main intention is, that the training component provides means for assuring that the machine learning model was not compromised since creation and is not produced by a unreliable source.

For the machine learning engine consequently the model attestation checker has the task to analyze the ascertained at least one machine learning model and the model attestation in order to check that the machine learning model is valid resp. trusted.

Only if this checking by the model attestation checker of the machine learning models trustworthiness is successful, the at least one machine learning model is considered for being used by the machine learning engine.

If this is the case then in the device the acquired input data are analyzed by the machine learning engine by means of the trusted machine learning model in order to achieve a results of the decision task.

As the decision task is based only on attested at least one machine learning models, the machine learning engine then further provides a result attestation for the decision output. The result attestation preferably is another digital signature.

The described method manages to achieve the goal of the invention as the result of the decision task provides an assurance about the at least one machine learning model that was made use of by the machine learning engine. Besides common security tasks of making tamper proof hardware, the contributed data for making the decision is not arbitrarily put together, but followed a defined approach, which is attested by providing the model attestation and finally the result attestation. With that, causative attacks on the system are prevented, or at least detected. With such a reliable result depending upon the use case the receiving party, e.g. a car that decides if it makes a full break, an authentication system which decides to give access to a person, etc. has accountable input for its carried out operations.

Furthermore the method uses common techniques like digital signatures, which only require organizational effort for deploying keys, and some processing resources. For a system making use of machine learning methods the processing power should anyhow be no issue.

According to a preferred embodiment of the invention it is propose that the training component further comprises a training attestation checker, the method further comprising the steps for the training attestation checker of
  acquiring training data,
  approving training data in case acquired training data comprise a data attestation,
for the training component:
  improving said at least one machine learning model only with training data approved by the training attestation checker,
  providing a model attestation to the at least one machine learning model.

This embodiment relates mainly to the training component which cares for the creation of the at least one machine learning model. The training component is created for acquiring a multitude of training data and to use them with a model learner to create or improve the machine learning model.

For assuring that the machine learning model is only created from reliable training data, the training component has a training attestation checker. In that sense only training data which comprise a data attestation are considered for feeding the model learner.

In a preferred embodiment the training data comprise a data attestation when the training data are supplied by a supervised content provider. As such the type of data collection is an indication about reliability of training data. As with a signature from the content provider it is assured who provided the data, the training component detect, if the data are provided by such supervised content providers or not. When only such supervised training data are signed, then no random data are allowed to enter into the training phase. This increases the accountability of the results.

According to this preferred embodiment, it is assured that as long as only training data comprising a data attestation are used, the resulting machine learning model is not compromised as well. Hence the training component will in this case provide a model attestation to the produced machine learning model. Such model attestation is then made use of for the decision making by the machine learning engine, as it is a precondition for providing a result attestation.

In another preferred embodiment it is suggested that the steps for the model attestation checker of:
  acquiring at least one set of input data
  checking if said set of input data is trusted by digital signature, for the device:
  considering for said decision making only input data that are trusted.

With this embodiment a third step of securing the result of the machine learning based decision task is carried out. Here the input data for the machine learning engine are checked if they are digitally signed. Such a signature is preferably provided by a respective sensor, in particular when not being part of the device itself.

This interface to the outside world is another vulnerability for hacking the device, whereas this does not exactly relate to causative attacks. Nonetheless when the device is expected to make a decision based on input data, the output will be unreliable—even when training data and the machine learning model are trusted—when it is not known if the sensor is reliable and/or if the data used by the machine learning engine are exactly those that are produced by the sensor.

When the device trusts signatures of a certain sensor, then it will see the input data by such a sensor as reliable. As a result the machine learning engine only refers to signed input data.

According to another preferred embodiment it is proposed that the machine learning engine is capable of using at least one of input data that are not signed and a machine learning model that is not attested, wherein in case at least one of the input data or the machine learning model is not trusted, omitting providing the decision output with a result attestation.

In this embodiment a scenario is proposed where both signed and unsigned data may be used in parallel by the machine learning engine. Such data may comprise the machine learning model or the input data. This encompasses machine learning engines which use only attested machine learning models, but any type of input data, and vice versa or any combination.

When this is the case, then the machine learning engine may produce a decision result which is either provided with a result attestation, or not. One option is, that the input data are never signed, but the machine learning model may be signed or not. In this option only the available model attestation drives if the result attestation is provided or not.

In a second aspect of the invention it is proposed a device for performing a decision task, comprising a machine learning engine and at least one interaction interface for retrieving at least one machine learning model from a training component, wherein the decision task is carried out with the machine learning engine, configured to use at least one machine learning model, the device further comprises an model attestation checker for controlling the at least one interaction interface of the machine learning engine, wherein the model attestation checker is configured to check if said machine learning model retrieved over the interaction interface is trusted by a model attestation, the machine learning engine is configured to consider for said decision making measure only said trusted machine learning model, and to provide a result attestation for the decision output.

In this aspect of the invention the device is part of a system comprising the device and the training component.

The device comprises appropriate processing circuitry for operating a machine learning engine. The machine learning engine is in particular a software program having access to volatile and/or permanent memory circuitry of the device. The permanent memory circuitry comprises the machine learning model, which is a data structure, in particular equipped with data access software library, like a database software. In particular dedicated software tools for providing speed optimized access to the machine learning model data are recommended.

Furthermore the device is equipped with an interaction interface with the training component, from where the device receives the at least one machine learning model.

The device further provides means for acquiring input data. Such means may encompass at least one sensor. Additionally or alternatively a data exchange interface, like a serial or parallel interface, resp. an USB port etc. is preferably available for providing the device with input data.

The device is configured to carry out a decision task by means of the machine learning data, whereas the decision task is to be carried out on the input data. Such decision task may comprise a response, if a person recorded by voice and/or picture belongs to the group of eligible people, where a plurality of training data relating to this group of persons is stored in the machine learning model.

The result would in this example be a person's name or identification, and preferably a rating how likely it is that the person recorded by the sensor data matched to the data in the machine learning model.

The device further comprises a model attestation checker, which is a software module checking the attestation of the at least one machine learning model received from the training component Preferably the device further comprising a result attestation component which is configured to provide a result attestation to the decision output in case the at least one machine learning model employed by the machine learning engine for performing the decision task is trusted by a model attestation.

The result attestation component is in particular a software component operating on the processing circuitry on the device. It is configured to check if the machine learning model is trusted thanks to a model attestation. Only if this is the case then it will provide a result attestation to the decision result. Such a result attestation is preferably another signature.

This assures that the receiver of the decision results receives an indication that the at least one machine learning model used for making the decision was created from trusted training data.

With the model attestation and the result attestation the decision task is consequently secured.

Preferably the device is configured that way that the model attestation checker is executing in a tamper proof environment being part of the device.

Such tamper resistant environment is preferably implemented by way of a secured hardware module, like a secure element. Alternatively a secured software environment is further suggested for tamper proofing the execution of the model attestation checker.

Such environment preferably comprises both areas of storing and of execution of the model attestation checker. Approaches like the sandbox concept or trusted computing are known to solve that requirement.

Additionally it is advantageous if more components are located in the tamper proof environment. This in particular relates to the machine learning engine, as well as parts of or the whole training component.

With this embodiment the device is further secured not only for causative attacks, but also for immediate attacks on the device's integrity itself.

Furthermore it is suggested that the device further being communicatively coupled to at least one training component comprising a training attestation checker and a training data acquisition interface, wherein the training data acquisition interface is configured to acquire training data, and the training attestation checker is configured to approve training data in case acquired training data comprise a data attestation, and the training component is configured to improve the machine learning model only with training data approved by the training attestation checker, and to provide a model attestation to the improved machine learning model.

This embodiment relates to the training component for creating or improving the at least one machine learning model, which is used by the machine learning engine of this device. In a preferred embodiment the training component is part of the device. In that case the software components comprised by the training component preferably are executed on the processing circuitry of the device. Alternatively the training component provides its own processing circuitry, preferably accompanied by sufficiently volatile and permanent memory circuitry.

Usually for the training phase other hardware resource requirements are needed than for the decision phase itself. In particular the amount of data to be processed may vary dramatically in favor of the training phase.

The training component provides a training data acquisition interface for receiving training data. This is preferably done by any kind of data exchange interface.

The training component furthermore comprises a training attestation checker. This is in particular a software module or application operating on the training component. The training attestation checker is configured to check if the training data provide data attestations. If this is the case the training attestation checker checks if the data attestations for each set of training data are valid. The latter is in particular the case for a data attestation by means of a digital signature. In that case the typical cryptographic operations are needed to be conducted in order to find out if the verification of the digital signature leads to a valid result.

If this is the case then the training attestation checker approves the usage of the training data for the training phase of the respective at least one machine learning model. If more than one machine learning model is maintained, the training data may be used for one or more of the respective machine learning models.

When the training phase has concluded, and only approved training data are used for training the machine learning models, then the training attestation checker is configured to provide a model attestation to the produced or improved at least one machine learning model.

In another preferred embodiment it is further proposed that the training data are further approved by the training attestation checker in case said training data encompass attested results from a machine learning engine using an attested machine learning model.

In this embodiment another way of acquiring training data is suggested. Here the result of a machine learning engine is used, provided it is attested. This relates in particular to the result of the respective device. Alternatively another instance of the same type of device may produce such attested result. According to this embodiment such data are accepted as valid training data, provided a valid results attestation is provided.

This embodiment appears like an infinitive loop. Nonetheless for certain use cases it is preferable to use the result data—in particular in conjunction with the input data—again for training purposes.

The second aspect of the invention shares the advantages of the first aspect of the invention.

As it is shown this invention advantageously solves the depicted problem and suggests a method and device for secured carrying out decision tasks based on machine learning. The invention provides the possibility to employ an end-to-end secured data stream, and as such introduces accountability for machine learning based decisions.

BRIEF DESCRIPTION OF THE DRAWINGS

The following description and the annexed drawings set forth in detail certain illustrative aspects and are indicative of but a few of the various ways in which the principles of the embodiments may be employed. Characteristics and advantages of the present invention will appear when reading the following description and annexed drawings of advantageous embodiments given as illustrative but not restrictive examples.

Figure 1:
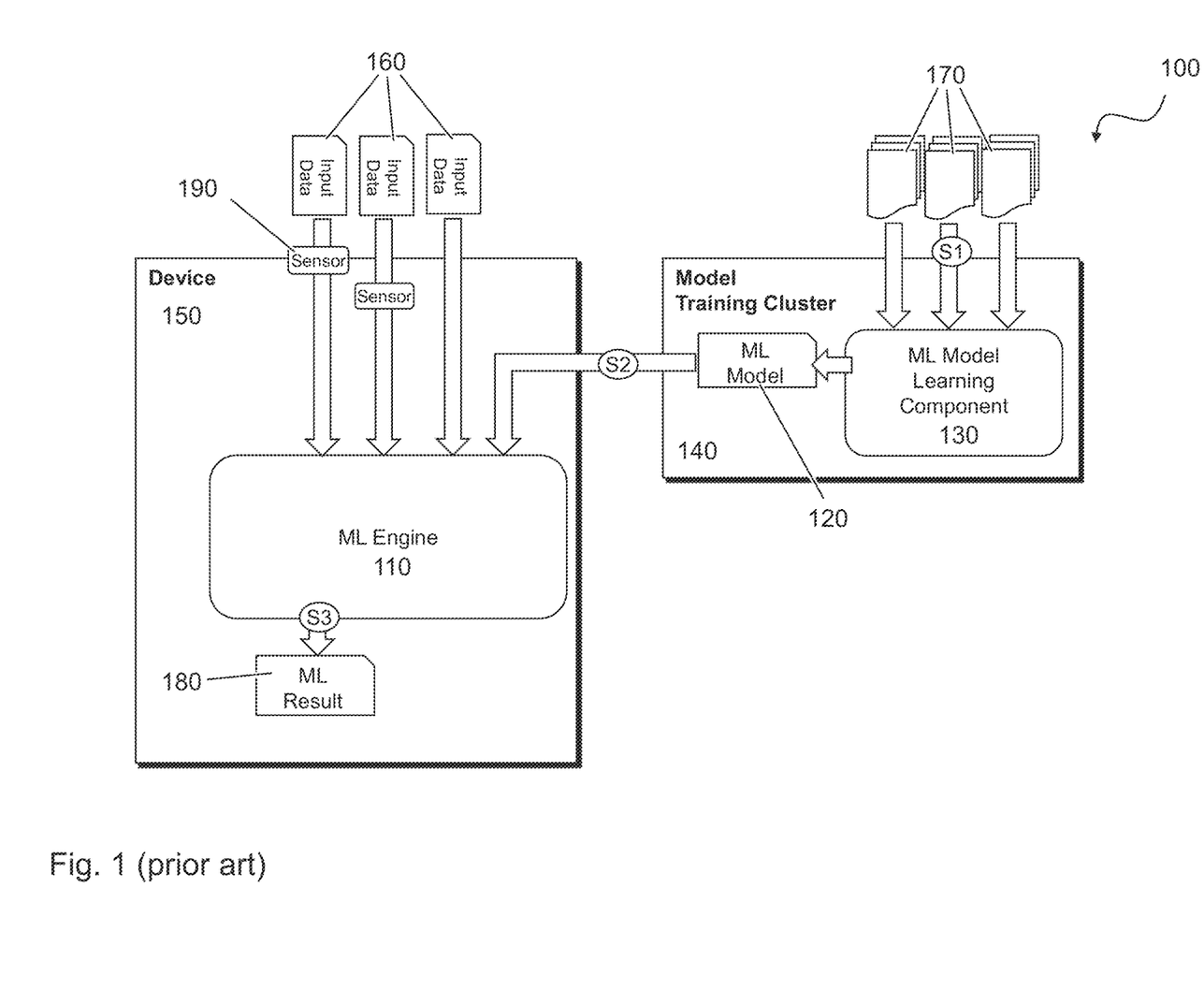
FIG. 1 represents a system of the type to which the present invention is applied according to the prior art.

FIG. 1 schematically shows a system 100 for machine learning based decision making according to the prior art. This system represents the typical components of a machine learning based decision system. As such a machine learning based decision system generally consists of a training component for creating a machine learning (ML) model and a decision component for making a decision by virtue of said ML model. In this exemplary embodiment these components are shown separately as model training cluster 140 and the device 150. This is an advantageous scenario as the training phase requires a lot of processing resources for handling the large amount of training data 170 that are used to create the ML model.

Such an ML model typically represents a data structure like a neuronal network that is getting more reliable by training with training data 170 retrieved via the first interface S1, the so-called training data acquisition interface. Such training data are typically real data with a qualification. E.g. for the use case of visual obstacle recognition the ML model learning component 130 is provided with images plus at least the qualification if an obstacle is visible on the image or not. The results of such training phase is represented in the at least one ML model 120.

The ML model 120 is then provided by means of an interaction interface S2 to the device 150, where a machine learning based decision is desired. Such device comprises in particular a machine learning engine 110. The device is configured to acquire a set of input data 160. Depending on the scenario, such input data acquisition is carried out by sensors 190, e.g. in the context of an obstacle recognition by optical sensors like camera. Further a combination of sensors, like optical and acoustical sensors is advantageous e.g. to gain a set of input data for increasing the reliability of the ML based decision. This is typically the case when a car collision is avoided, as the sound of brakes might increase the reliability of the collision detection.

The outcome for a set of input data 160 handled by the machine learning engine 110, equipped with at least one ML model 120, is a ML result 180, which is provided via result interface S3. This is typically a decision, preferably enriched with a rating. Such a rating then indicates the reliability of the machine learning based decision. If a perfect match is done, e.g. in case of textual recognition, the rating is obviously very high, if no clear decision is retrieved, then the rating is rather low.

With such information, the system which works on the machine learning based decision making engine is put into the position to handle accordingly. Such handling strongly depends on the use case. For a collision avoidance it is the question, if an automated braking is carried out or not.

However, when no clear decision with high reliability is achieved, then the system needs to handle this accordingly. If applicable, then an intermediate action is carried out, like a warning sound to the driver, a soft braking etc. in the case of collision avoidance. In the case of optical recognition for authentication purposes, e.g. a door opener etc., then an additional security measure could be applied.

All this is part of the environment of machine learning based decision making. However, it becomes clear, that the decisions, which might have big impact, strongly depend on the ML model, and consequently on the training data. It is therefore the question how can the system be sure, that such content is really what it claims to be.

For that the inventive solution is designed for, where an exemplifying embodiment, analogue to the prior art described before, is shown in FIG. 2.

Figure 2:
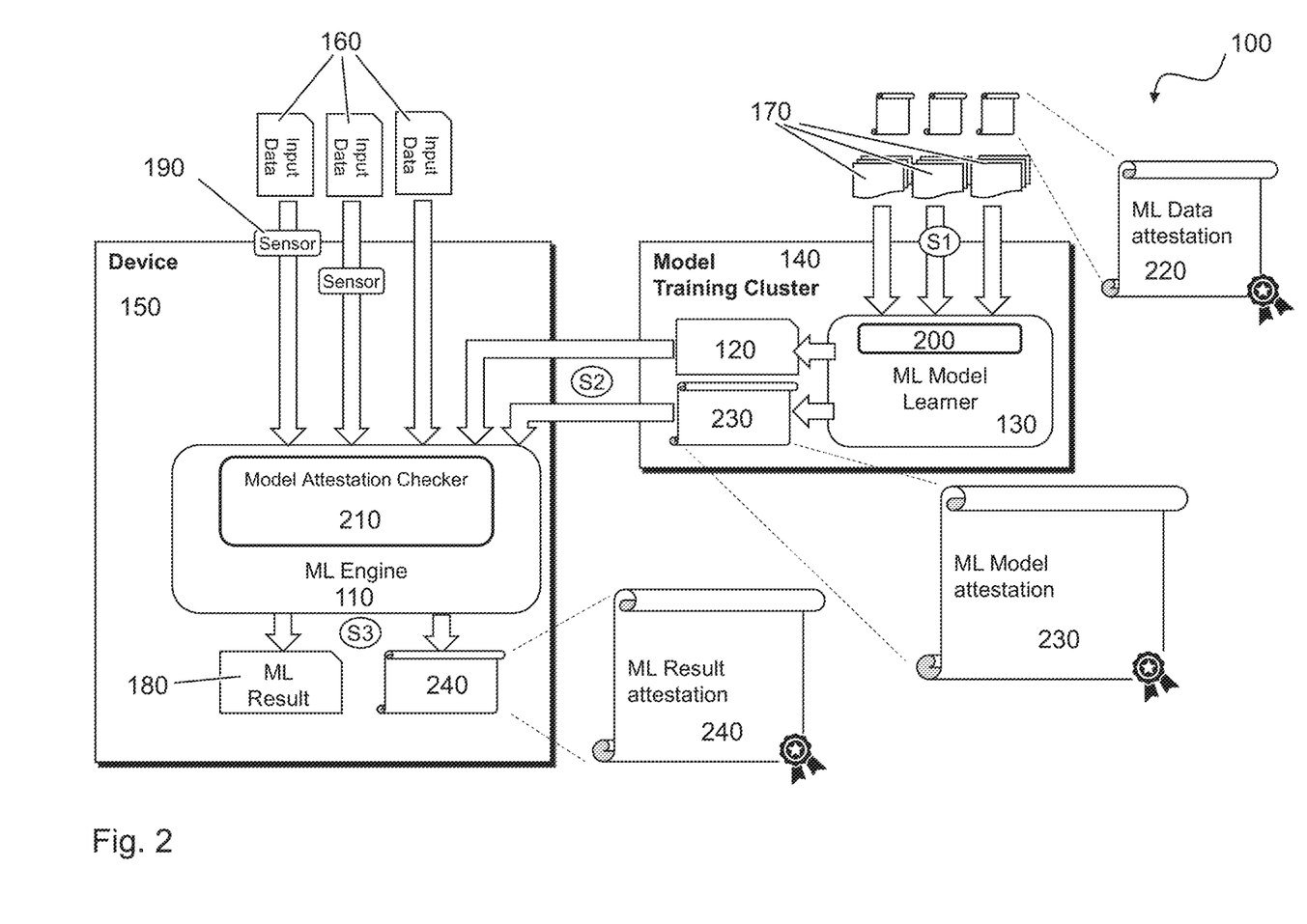
FIG. 2 represents a system of the type to which the present invention is applied to as an embodiment.

Here it is shown a similar system 100 comprising basically the same building blocks of the model training cluster 140 comprising the ML model learner 130, as well as the device 150 comprising the ML engine 110, wherein via an interaction interface S2 the ML model learner provides a ML model 120 to the ML engine 110.

The difference starts with the acquisition of the training data 170 via the training data acquisition interface S1. The system according to the invention is suspicious relating to the reliability of the training data. Hence the ML model learner 130 additionally comprises a training attestation checker 200. Such training attestation checker features a kind of training data filter. Only training data that are proven to be reliably created are accepted. To prove reliability is carried out by adding a ML data attestation 220, which is preferably a digital signature for identifying the source of the data. When a data source is known to carry out supervised training data, then a digital signature for the data indicates first, that the training data are sourced from said data source, and second that they are not modified before reception at the ML Model learner 130. This gives enough of accountability of the training data. Hence the training attestation checker 200 will allow processing of such data.

Supervised creation of training data comprises e.g. that the qualification of training data, e.g. that a person visible on a picture is really the depicted person according to the qualification, is double checked and assured. In the scenario of authentication by optical face recognition a hacker could easily try to manipulate the system by introducing pictures of his face (or other biometric images) and qualify it with another person's identify which is supposed to be eligible for access. If such data is not supervised, then it is practically impossible to find out such manipulation. If a data sourcing entity can provide proofs that such manipulation is technically avoided, or will at least not be undetected, then the data sourcing entities signature of the training data will be understood as reliable. As a digital signature requires sharing of the public keys for the cryptographic operation of signing and verifying, only public keys of reliable sources are maintained at the training attestation checker 200.

If such reliable signature resp. ML data attestation 220 is available, then the training attestation checker 200 will approve that such signed training data are used in the ML model learner 130.

With the ML model learner the training data are processed for creating at least one ML model 120. As indicated with the constellation of a separate model training cluster and device, where the machine learning based decision is carried out, another vulnerability becomes apparent. This is the interaction interface S2 between the model training cluster and the device, that is the interface where the created ML model 120 is provided to the device.

Hence according to the shown embodiment of the invention this issue is addressed by adding a ML model attestation 230, preferably another signature for the ML model 120. With the signature the ML model learner approves that the ML model was only created by using training data 170 that were attested, that is trusted.

So the device 150 receives a signed ML model which is then used by the ML engine 110.

But even when both components are not separated, there is still a possibility to manipulate a stored ML model. Hence it is preferable that the ML model is stored in a secured environment after its signature is checked.

For addressing that the device 150 wants to rely on the ML result 180 produced by the ML engine, consequently also the ML result 180 is equipped with a ML result attestation 240. Preferably again another signature is provided by the ML engine resp. the Model attestation checker 210, with which it is confirmed that only an attested ML model was used, which is only the case if only attested training data were used for creating the ML model.

In other words, an end-to-end attestation is provided that assures that the ML result was not affected by causative attacks and can be relied upon by the device that is handling the ML result.

Figure 3:
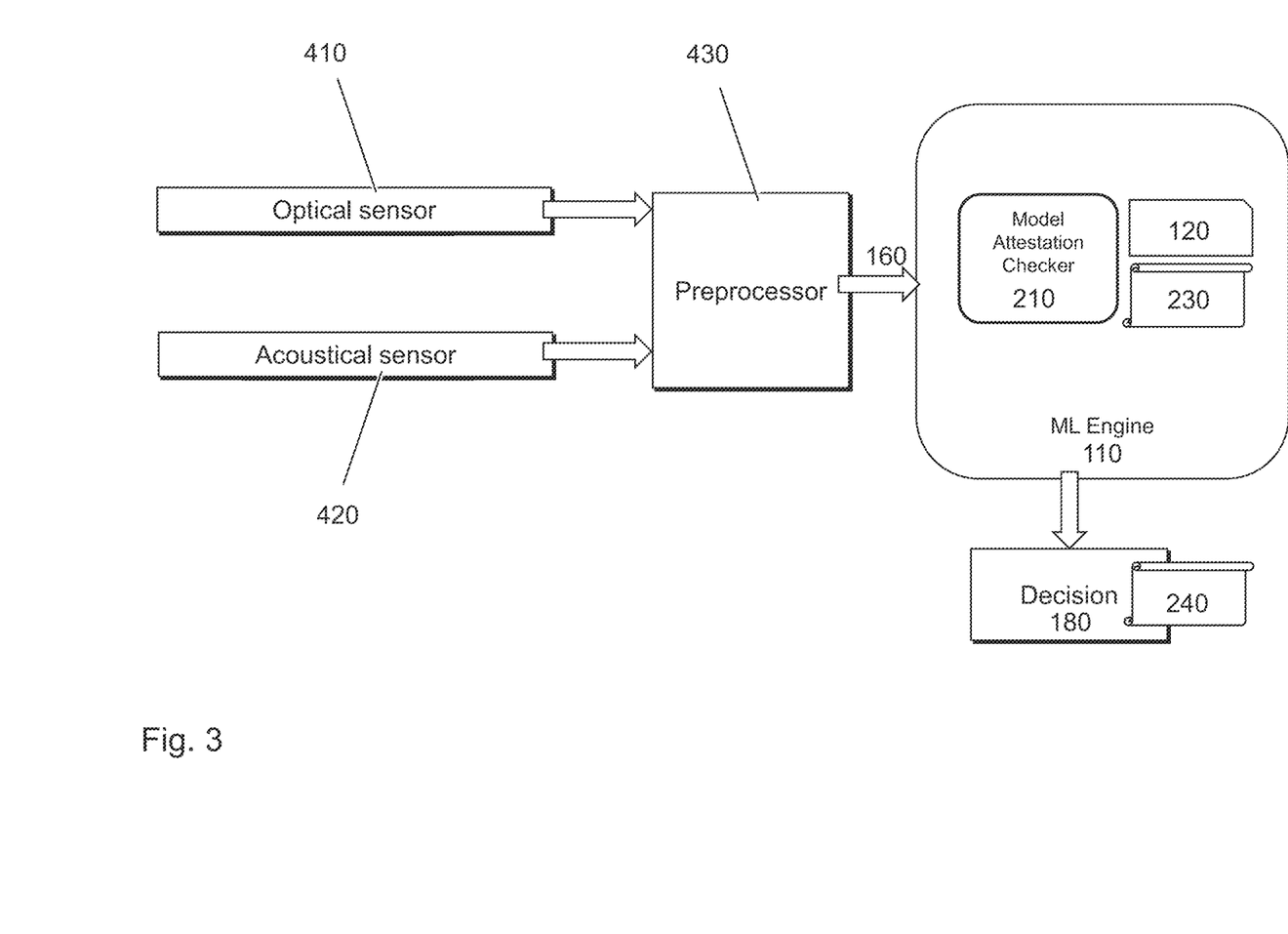
FIG. 3 shows another exemplifying embodiment of present invention.
Figure 4:
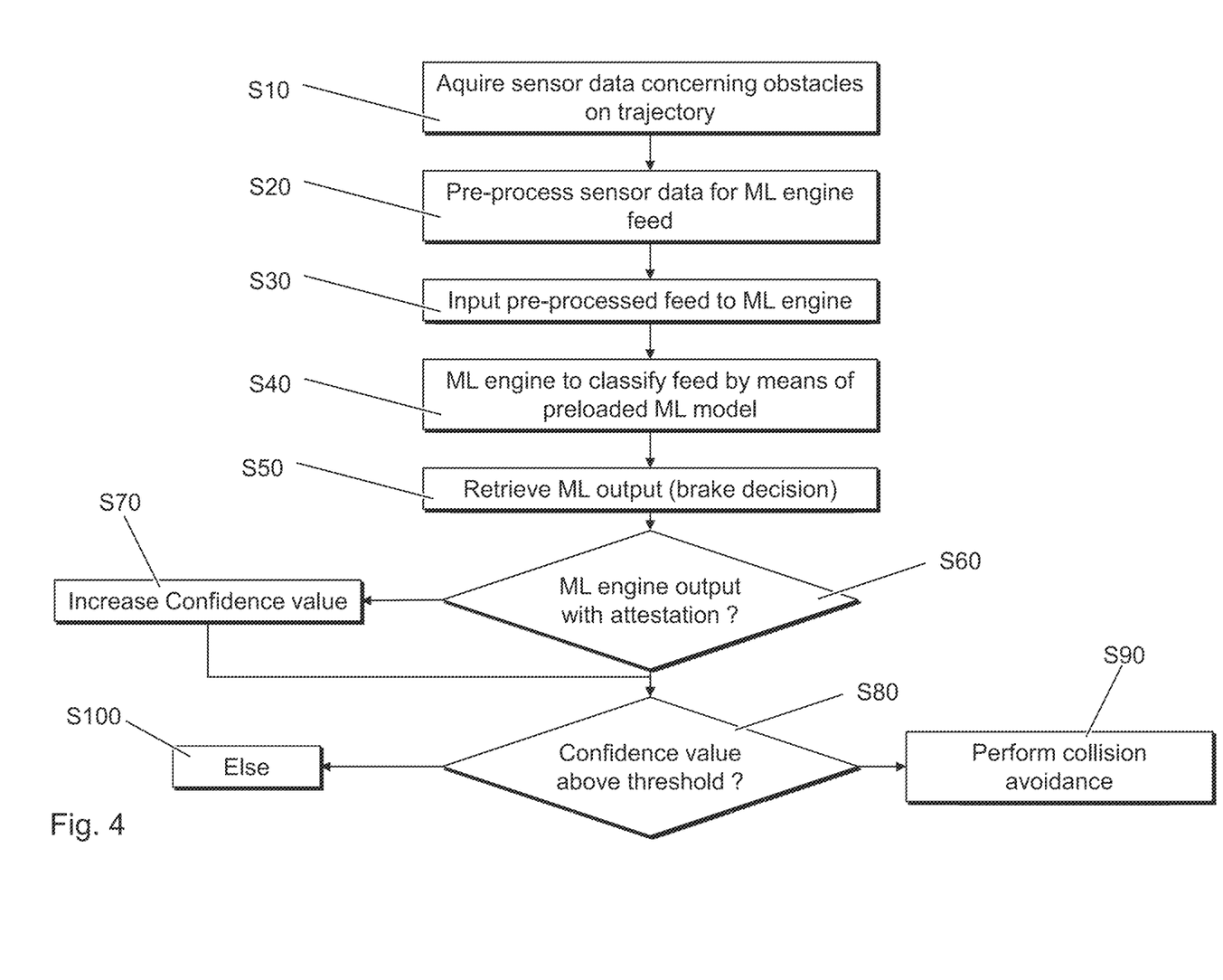
FIG. 4 shows a flow chart representing an embodiment of the present invention.

FIGS. 3 and 4 shows in an exemplifying embodiment in the workflow how to use the inventive system and method for using a ML based system for obstacle recognition, e.g. in a vehicle.

FIG. 3 shows the setup of the system as a device, e.g. being part of a vehicle. Here sensor data are acquired that could concern obstacles on a planned trajectory. Preferably such sensors comprise optical sensors like cameras, but also acoustic, infrared, echo sounder sensors etc. could be used. The shown vehicle is equipped with an optical sensor 410 and an acoustical sensor 420. Each of these sensors creates proprietary raw data. In a preprocessor 430 such raw data from the different sensors are combined and converted to a feed of the input data 160 for the ML engine 110. In the ML engine 110 the data are then handled by virtue of a preloaded ML model 120. This ML model is equipped with a model attestation 230, like a signature. The model attestation checker 210 checks the model attestation in order to figure out, if the ML model is reliable. If so, the output decision 180 of the ML engine is in this case as well equipped with a ML result attestation 240.

The whole process is shown in the flowcharts of FIG. 4.

The workflow starts for the device in step S10. Each of these sensors creates proprietary raw data relating to obstacles on the trajectory in step S10. In steps S20 and S30 the raw data are preprocessed and handed over as input data to the ML engine, equipped with at least one ML model. Preferably more than one ML Model is used, as this would allow a step by step detection for increasing the hit rate.

With this preloaded ML model the input data feed is used for classifying the input data, as indicated in step S40. After doing so the ML engine provides an output with a decision recommendation for the device. In this case step S50 produces a brake decision. That means, the ML engine found based on the input data in combination with the experiences collected in the ML model, that the sensors indicate an obstacle on the planned trajectory of the vehicle. For avoiding a collision hence the ML engine recommends to the vehicle to actuate the brake.

The device however checks first in step S60 if the output of the ML engine additionally provides a result attestation. Such a result attestation may depending upon the implementation comprise attestation of test data as well.

One way of providing a result attestation is adding a digital signature to the ML engine's output.

If this is the case, the confidence value of the decision output is increased. That means the recommendation from the ML engine gets a higher accountability, as it is obviously based on a reliable ML model based on reliable training data. However, the signature is not the only indicator for confidence. First the ML model itself may be in the position to provide a rating, how sure the obstacle detection is. Second, an indication about the condition of the sensors is preferably used as well. If one of the many sensors is out of service, or somehow interrupted, the decision might be based on less input data.

Hence in the end the device checks in step S80 if the confidence value is above a predefined threshold. If this is the case, then the recommendation from the ML engine is followed, which means in this case a collision avoidance is carried out, in particular by automatic activating the brakes (S90). Otherwise the confidence is not sufficiently high enough, and other options might be taken by the vehicle in step S100. A warning to the driver could be an option, but this is very much related to the use case, and outside the scope of this invention.

In the above detailed description, reference is made to the accompanying drawings that show, by way of illustration, specific embodiments in which the invention may be practiced. These embodiments are described in sufficient detail to enable those skilled in the art to practice the invention. It is to be understood that the various embodiments of the invention, although different, are not necessarily mutually exclusive. For example, a particular feature, structure, or characteristic described herein in connection with one embodiment may be implemented within other embodiments without departing from the scope of the invention. In addition, it is to be understood that the location or arrangement of individual elements within each disclosed embodiment may be. The above detailed description is, therefore, not to be taken in a limiting sense, and the scope of the present invention is defined only by the appended claims, appropriately interpreted, along with the full range of equivalents to which the claims are entitled.

The invention claimed is:

1. A method for securing a system configured to perform decision tasks carried out by a machine learning engine, equipped for operating with at least one machine learning model,
the system comprising at least one training component for improving the at least one machine learning model, a device for carrying out decisions based on said machine learning model and a set of input data, and an interaction interface for exchanging said at least one machine learning model between training component and device, wherein the device comprises a model attestation checker, wherein the method comprises the steps of:
for the device:
acquiring input data,
ascertaining at least one machine learning model over the interaction interface, for the model attestation checker:
checking if said at least one machine learning model is trusted by a model attestation,
considering by the machine learning engine, for decision making, only those machine learning models that are trusted,
for the machine learning engine:
carrying out the decision task for acquired input data by using said at least one trusted machine learning model,
providing a result attestation for the decision output.

2. The method according to claim 1,
wherein the training component further comprises a training attestation checker, the method further comprising the steps for the training attestation checker of:
acquiring training data,
approving training data in case acquired training data comprise a data attestation, for the training component:
improving said at least one machine learning model only with training data approved by the training attestation checker,
providing a model attestation to the at least one machine learning model.

3. The method according to claim 2,
the method further comprising the steps for the model attestation checker of:
acquiring at least one set of input data,
checking if said set of input data is trusted by digital signature, and for the device:
considering for said decision making only input data that are trusted.

4. The method according to claim 1,
wherein the training data comprise a data attestation when training data are supplied by a supervised content provider.

5. The method according to claim 1,
wherein the machine learning engine is capable of using at least one of input data that are not signed and a machine learning model that is not attested,
wherein in case at least one of the input data or the machine learning model is not trusted, omitting providing the decision output with a result attestation.

6. A device for performing a decision task, comprising a machine learning engine and at least one interaction interface for retrieving at least one machine learning model from a training component,
wherein the decision task is carried out with the machine learning engine, configured to use at least one machine learning model,
the device further comprises a model attestation checker for controlling the at least one interaction interface of the machine learning engine,
wherein the model attestation checker is configured to check if said machine learning model retrieved over the interaction interface is trusted by a model attestation, and
the machine learning engine is configured to consider, for decision making, only said trusted machine learning model, and to provide a result attestation for a decision output.

7. The device according to claim 6,
wherein the device is further configured to retrieve at least one set of input data, and the model attestation checker is configured to check if said set of input data is trusted by a digital signature,
and the machine learning engine is configured to consider for said decision making measure only a trusted input data.

8. The device according to claim 6,
wherein the model attestation checker is executed in a tamper proof environment being part of the device.

9. The device according to claim 6,
further comprising a result attestation component which is configured to provide a result attestation to the decision output in case the at least one machine learning model employed by the machine learning engine for performing the decision task is trusted by a model attestation.

10. The device according to claim 6,
further being communicatively coupled to at least one training component comprising a training attestation checker and a training data acquisition interface,
wherein the training data acquisition interface is configured to acquire training data,
the training attestation checker is configured to approve training data in case acquired training data comprise a data attestation,
and the training component is configured to improve the machine learning model only with training data approved by the training attestation checker,
and to provide a model attestation to the improved machine learning model.

11. The device according to claim 10, wherein the training component is part of the device.

12. The device according to claim 10,
wherein the training data are further approved by the training attestation checker when the training data are supplied by a supervised content provider.

13. The device according to claim 10,
wherein the training data are further approved by the training attestation checker in case said training data encompass attested results from a machine learning engine using an attested machine learning model.

14. The device according to claim 6,
wherein the machine learning engine is capable of using at least one of input data that are not signed and a machine learning model that is not attested,
wherein in case at least one of the input data or the machine learning model is not trusted, the device is configured to omit providing a result attestation to the decision output.

15. The method of claim 3, wherein the securing of said system sequentially implicates two levels of attestation, consisting of:
training data attestation, provided through the training attestation checker by way of certificate based attestation; and
model attestation, provided through the model attestation checker by way of certificate based attestation,
wherein when said training data attestation is available, then the training attestation checker approves signed training data for use in the machine learning model; and
thereafter,
wherein when said model attestation confirms a reliability of the machine learning model, it provides assurances that the machine learning model, and training data used therein, was not compromised since creation and is not produced by an unreliable source.

* * * * *